US00PP16141P3

(12) United States Plant Patent
Hofmann

(10) Patent No.: US PP16,141 P3
(45) Date of Patent: Dec. 6, 2005

(54) **NEW GUINEA *IMPATIENS* PLANT NAMED 'FISNICS BURGSWEET'**

(50) Latin Name: *Impatiens hawkeri*
Varietal Denomination: Fisnics Burgsweet

(75) Inventor: Birgit C. Hofmann, Bendorf (DE)

(73) Assignee: Florfis AG (CH)

( * ) Notice: Subject to any disclaimer, the term of this patent is extended or adjusted under 35 U.S.C. 154(b) by 120 days.

(21) Appl. No.: 10/829,352

(22) Filed: Apr. 22, 2004

(65) Prior Publication Data

US 2004/0244085 P1 Dec. 2, 2004

(30) Foreign Application Priority Data

Apr. 22, 2003 (CH) ..... 03-1991

(51) Int. Cl.[7] ..... A01H 5/00

(52) U.S. Cl. ..... Plt./318

(58) Field of Search ..... Plt./318

*Primary Examiner*—Kent Bell

(74) *Attorney, Agent, or Firm*—Foley & Lardner, LLP

(57) ABSTRACT

A new and distinct cultivar of New Guinea *Impatiens* plant named 'Fisnics Burgsweet', and particularly characterized by the combined features of lavender and purple bi-colored flower color; medium to large, round, almost flat flowers borne well above the foliage; uniform, dark green foliage, relatively wide leaves; medium sized to larger, round and bushy plant habit; and early to medium flowering response.

1 Drawing Sheet

Genus and species of the plant claimed: *Impatiens hawkeri*.

Variety denomination: 'Fisnics Burgsweet'.

BACKGROUND OF THE INVENTION

The present invention comprises a new and distinct cultivar of New Guinea *Impatiens* plant, botanically known as *Impatiens hawkeri*, and hereinafter referred to by the cultivar name 'Fisnics Burgsweet'.

'Fisnics Burgsweet' is the product of a planned breeding program and originated from a hybridization made by the inventor, Birgit C. Hofmann, in a controlled breeding program in Hillscheid, Germany, in 2000.

The female parent was the variety 'Harmony Raspberry Cream' (unpatented), which is characterized by white to light pink flower color with cherry red stripes on petals, very dark, almost black, foliage, and medium sized plant habit.

The male parent of 'Fisnics Burgsweet' was 'Kispix' (unpatented), having pink and red bi-colored flowers, medium green foliage, and approximately medium sized plant habit.

'Fisnics Burgsweet' was discovered and selected as one flowering plant within the progeny of the stated cross by the inventor in April, 2001 in a greenhouse in Galdar, Gran Canaria, Spain.

The first act of asexual reproduction of 'Fisnics Burgsweet' was accomplished when vegetative cuttings were taken from the initial selection in July 2001 in a controlled environment in Galdar, Gran Canaria, Spain, by, or under the supervision of the inventor.

Horticultural examination of plants grown from these cuttings initiated in the spring of 2002 in Hillscheid, Germany, and continuing thereafter, has demonstrated that the combination of characteristics as herein disclosed for 'Fisnics Burgsweet' are firmly fixed and are retained through successive generations of asexual reproduction. The new cultivar reproduces true to type.

'Fisnics Burgsweet' has not been observed under all possible environmental conditions. The phenotype may vary significantly with variations in environment such as temperature, light intensity and day length, without, however, any variation in genotype. The following observations, measurements, and comparisons describe plants grown in Hillscheid, Federal Republic of Germany, under greenhouse conditions which approximate those generally used in commercial practice.

BRIEF SUMMARY OF THE INVENTION

The following traits have been repeatedly observed and are determined to be basic characteristics of 'Fisnics Burgsweet', which in combination distinguish this *Impatiens* as a new and distinct cultivar:

1. Lavender and purple bi-colored flower color;
2. Medium to large, round, almost flat flowers borne well above the foliage;
3. Uniform, dark green foliage, relatively wide leaves;
4. Medium sized to larger, round and bushy plant habit; and
5. Early to medium flowering response.

Of the many commercial cultivars known to the inventor, the most similar in comparison to 'Fisnics Burgsweet' is the parental variety 'Kispix' and the variety 'Fisimp 172' (U.S. Plant Pat. No. 13,699).

In comparison to 'Kispix', 'Fisnics Burgsweet' has a more purple-violet flower color whereas 'Kispix' has pink flowers, as well as wider and more blurred red-purple pattern of secondary flower color, and darker green foliage.

In comparison to 'Fisimp 172', 'Fisnics Burgsweet' has a more blurred pattern of secondary petal color, while 'Fisimp 172' has narrow, but distinct reddish stripes. Furthermore, 'Fisnics Burgsweet' has longer peduncles, darker and more glossy foliage, more even and better branched plant habit.

BRIEF DESCRIPTION OF THE DRAWING

The accompanying photographic drawing shows typical flower and foliage characteristics of 'Fisnics Burgsweet' with colors being as true as possible with illustrations of this type.

The photographic drawing shows a side view of a typical flowering plant of 'Fisnics Burgsweet'.

DETAILED BOTANICAL DESCRIPTION

In the following description color references are made to The Royal Horticultural Society Colour Chart (R.H.S.). The color values were determined indoors from plants growing in a greenhouse in May 2003, Hillscheid, Germany.

The description is based on plants which were planted as rooted cuttings in 12 cm pots in late February 2003, and then grown in the greenhouse at a minimum temperature of 16° C. Most observations and measurements were made after the beginning of flowering in mid May, when the plants were about 12 weeks old.

PLANT

General appearance and form:

*Plant habit.*—Medium sized to larger, round, bushy, and well-branched; growth is indeterminate, though weak after beginning of flowering.

*Height.*—18.0 cm.

*Width.*—27.7 cm.

*Number of branches.*—10–12.

*Length of branches.*—12–15 cm.

*Internode length.*—5.5–7.0 cm.

*Diameter of branches.*—5–7 mm.

*Stem color.*—Partly reddish-brown, RHS 182 B, partly green, RHS 143 C.

*Propagation.*—Terminal tips for cuttings.

*Rooting.*—Roots initiate in about 18 days at 22° C., from sticking to transplanting.

*Cultivation time.*—It takes about 9–10 weeks of growing time to produce a marketable flowering plant in a 12 cm pot.

Foliage:

*Leaf arrangement.*—Primarily in whorls.

*Shape of leaf.*—Elliptic, with acute base and acuminate tip.

*Surface.*—Glossy and smooth, with very faint pubescence.

*Margin.*—Slightly serrated, ciliated.

*Leaf length.*—11.5 cm.

*Leaf width.*—4.75 cm.

*Leaf blade upper surface color.*—Dark green, uniform; mature and young leaves between darker than but closest to RHS 139 A and 147 A.

*Veins on upper surface.*—RHS 53 A to 53 B.

*Leaf blade lower surface.*—Mainly purple, RHS 187 C, partly mixed with green, RHS 139 C; young leaves purple without green.

*Veins on lower surface.*—RHS 187 B.

*Petiole size.*—2.5 cm in length, 2–3 mm in diameter.

*Petiole color.*—Upper side RHS 53 D, lower side RHS 187 B.

INFLORESCENCE

*Flowering response.*—About 9 weeks after planting of rooted cuttings.

*Flowering season.*—Generally indeterminate, mainly from March to October, depending on light intensity.

Flower:

*Number of flowers per node.*—7–9, in various stages of development.

*Form of corolla.*—Single-type, 5 petals.

*Shape of corolla.*—Nearly round, butterfly-shape, relatively large for a bi-colored variety.

*Corolla size.*—Average length: 67 mm. Average width: 67 mm. Depth of corolla: 10–15 mm.

*Shape of petals.*—Cordate, only shallow lobes at the top end, base attenuate. Top petal: 26 mm long, 49 mm wide. Lateral petals: 29–30 mm long, 35 mm wide. Lower petals 30 mm long, 39 mm wide.

*Texture.*—Smooth, velvety.

*Aspect.*—Mostly flat, lateral petals may be slanting upright.

*Color (general tonality from a distance of three meters).*—Bi-colored, lavender-pink with purple pattern.

*Color of upper surface.*—RHS N74 C to RHS N74D ground color, stripes and splotch on top petal RHS N74 A.

*Color of eye zone.*—RHS 66 A.

*Color of lower surface.*—RHS N66 B.

*Spur.*—Downwardly curved, 6.5 cm long, 3 mm in diameter at the flower end; color pink, RHS 58 C, fading towards the tip.

*Peduncle.*—Approximately 5.7 cm in length, 2 mm in diameter; color light green, RHS 145 B to 145 C.

*Flower bud.*—Ovoid shape, 23 mm in length, 17 mm in width; color RHS N66 B.

Reproductive organs:

*Stamens.*—5 in number, upper surface color between RHS 66 A and RHS N74 A.

*Anthers.*—Fused, hooded.

*Pollen.*—Whitish-yellow, about RHS 8 D.

*Style and stigma.*—5 in number, very short, purple, about RHS 187 D.

*Ovary.*—5-celled, 5 mm long, surface dark purple, RHS 187 A.

Disease/pest resistance/susceptibility: No observations to date.

I claim:

1. A new and distinct cultivar of New Guinea *Impatiens* plant named 'Fisnics Burgsweet' as described and illustrated herein.

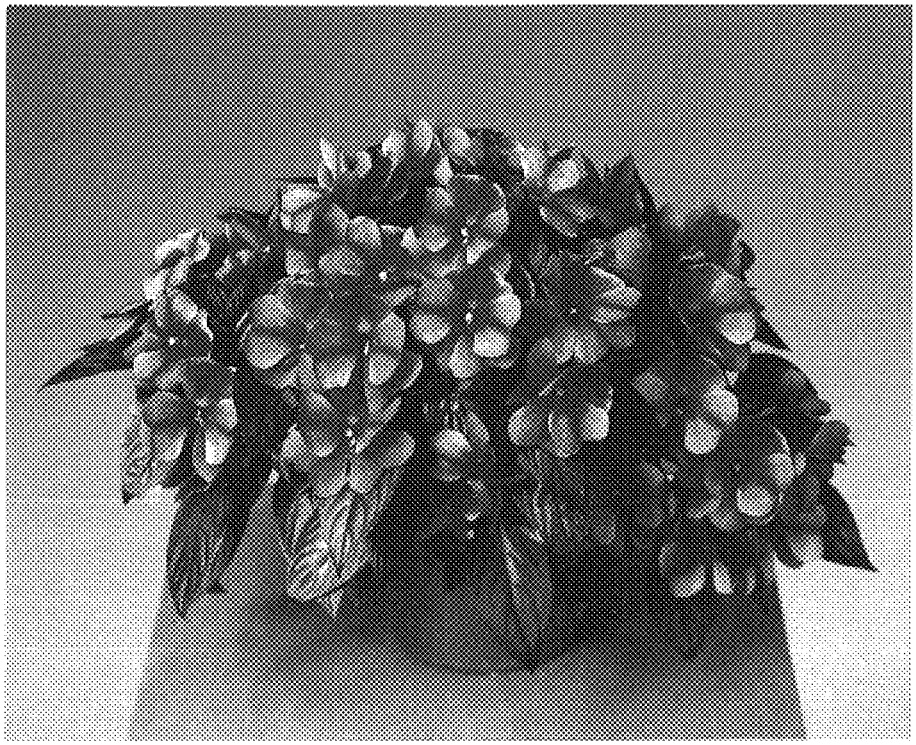

* * * * *